United States Patent [19]

Allen et al.

[11] Patent Number: 4,595,656

[45] Date of Patent: Jun. 17, 1986

[54] COUPLING AGENTS AND PRODUCTS PRODUCED THEREFROM

[75] Inventors: Stephen D. Allen, Park City, Utah; Michael Thompson, Evansville, Ind.

[73] Assignee: Becton Dickinson & Company, Paramus, N.J.

[21] Appl. No.: 568,698

[22] Filed: Jan. 6, 1984

[51] Int. Cl.$^4$ .................. G01N 33/53; G01N 33/549; G01N 33/533; A61K 49/00

[52] U.S. Cl. ......................... 435/7; 424/1.1; 424/9; 436/500; 436/532; 436/546; 436/547; 436/800; 436/804

[58] Field of Search ............... 436/500, 532, 537, 546, 436/547, 800, 804; 435/7; 424/1.1, 9

[56] References Cited

U.S. PATENT DOCUMENTS

| | | |
|---|---|---|
| 3,759,890 | 9/1973 | Wilson ............................. 436/513 |
| 4,119,589 | 10/1978 | Horn et al. ....................... 436/532 |
| 4,152,411 | 5/1979 | Schall, Jr. ........................ 436/546 |
| 4,279,992 | 7/1981 | Boguslaski et al. ................ 435/7 |
| 4,378,428 | 3/1983 | Farina et al. ..................... 435/7 |
| 4,426,453 | 1/1984 | Cree et al. ....................... 436/500 |
| 4,442,204 | 4/1984 | Greenquist et al. ............... 436/537 |
| 4,469,797 | 9/1984 | Albarella ......................... 436/537 |
| 4,476,228 | 10/1984 | Huchzermeier et al. ........... 436/500 |
| 4,476,229 | 10/1984 | Fino et al. ........................ 436/500 |
| 4,489,165 | 12/1984 | Wagner et al. ................... 436/537 |

*Primary Examiner*—Christine M. Nucker
*Attorney, Agent, or Firm*—Elliot M. Olstein

[57] ABSTRACT

Isocyanate or isothiocyanate substituted lactone or thiolactone is employed for coupling one organic compound to another. For example, such coupling agents can be employed for coupling thyroxine or digoxin to a fluorescent compound for use as a tracer in an assay.

18 Claims, No Drawings

COUPLING AGENTS AND PRODUCTS PRODUCED THEREFROM

This invention relates to compounds useful for coupling one organic material to another, intermediates useful in producing coupled products, and uses therefor.

In many cases, there is a need to couple one organic material to another, and in many cases, such coupling is accomplished by use of a bifunctional compound, often referred to as a coupling agent or spacer compound.

For example, in an assay such as an immunoassay, one of the components of the assay is a tracer which is comprised of a ligand such as an antigen, coupled to a suitable marker; e.g., a chromogen, such as a fluorescent dye. In producing such a tracer, in many cases, the antigen is coupled to the fluorescent dye by use of a bifunctional coupling agent or spacer compound.

Similarly, in an immunoassay employing a solid support there is a need to couple a material used in the assay, such as an antibody, to a solid support, such as a polymer, and in some cases, this is accomplished by use of a coupling agent.

There is need in the art for improved means of coupling one material to another through a coupling agent or spacer compound.

In accordance with one aspect of the present invention, there is provided bifunctional compounds which are useful as coupling agents.

In accordance with another aspect of the present invention, there is provided intermediates for coupling one material to another.

In accordance with a further aspect of the invention, there is provided coupled compounds or materials.

In accordance with yet another aspect of the invention, there is provided a process for preparing such coupling agents, intermediates and coupled compounds.

In accordance with a still further aspect of the present invention, there is provided a process for using the coupling agents, intermediates and coupled products.

More particularly, in accordance with one aspect of the present invention, there is provided coupling agents having the following structural formula:

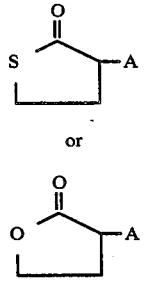

I or

II wherein A is
—N=C=S
or
—N=C=O

The coupling agents are bifunctional and the isocyanate and/or isothiocyanate functional group are capable of reacting with an active hydrogen substituent group of an organic compound to produce a coupled intermediate. In particular, an isocyanate group is capable of reacting with mercapto (thiol), hydroxy, carbonyl or primary or secondary amine functional groups, or appropriate salts thereto. Isothiocyanate may react with a primary or secondary amine group.

The reaction of coupling agent I or II with an appropriate organic compound produces the following coupled intermediates

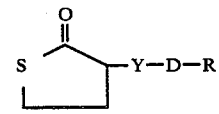

III

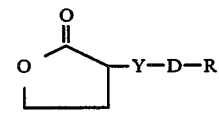

IV wherein Y is

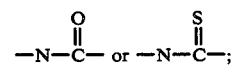

R is an organic radical and when Y is

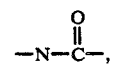

D is —O—; —S—;

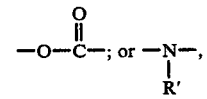

and when Y is

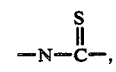

D is

and R' is hydrogen or a hydrocarbon radical preferably alkyl.

As should be apparent, D is derived from an active hydrogen substituent group on the organic compound to which compound I or II is coupled.

The lactone functional group of the intermediates of structural formulas III and IV is capable of reacting with organic compounds, which include at least one functional group which is a primary amine (aromatic or aliphatic primary amine, preferably aliphatic primary amine). The isocyanate or isothiocyanate functional group of the coupling compounds represented by structural formulas I and II is reacted first; and then the lactone functionality is reacted. Accordingly, a coupled compound produced in accordance with the present invention has the following structural formula:

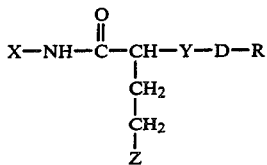

V wherein X is an organic radical; Y D and R are as previously defined and Z is —SH or —OH.

The coupling agents of the present invention may be prepared by reacting either D, L-homocysteinthiolactone or alpha-amino-γ-butyrolactone with either diphosgene or phosgene (to provide the isothiocyanate functional group) or thiophosgene (to provide the isothiocyanate functional group) in a suitable anhydrous solvent: e.g., anhydrous diozane, at an elevated temperature (e.g., reflux condition) for a time sufficient to complete the reaction. The solvent is then removed from the coupling agent. The product may be separated from unreacted starting material by dissolving the product in a solvent such as methylene chloride, followed by filtering the unreacted starting material.

The isocyanate or isothiocyanate functionality of the coupling agent of the present invention is coupled to an organic compound having an active hydrogen group, and in particular, at least one functional group as hereinabove described. Such coupling is accomplished by procedures generally known in the art for reacting an isocyanate or isothiocyanate group with an active hydrogen group. As known in the art, such coupling, in most cases, can be accomplished by mixing at room temperature or slightly elevated temperatures, followed by separation of the coupled compound from starting material.

Thus, in accordance with the present invention, the coupling agents represented by structural formulas I and II are initially reacted with an organic compound having an active hydrogen group, which organic compound is capable of being reacted with the isocyanate or isothiocyanate functional group. As a result, the organic compound which is reacted with the isocyanate functional group is generally other than a protein, in that proteins are generally not capable of being reacted under anhydrous conditions.

The coupled intermediates represented by structural formulas III and IV may be employed for producing a coupled product, as represented by structural formula V. In producing coupled products of the present invention, the lactone or thiolactone functional portion of Compound III or IV is reacted with an organic compound which includes at least one functional group which is a primary amine.

The intermediates of structural formula III or IV may be reacted in solution with an organic compound having a primary amine functional group to produce coupled compounds having structural formula V. In general, the reaction is effected at basic conditions and at temperatures from room temperature up to 100° C., although higher temperatures could be employed provided that such temperatures do not adversely affect the coupled compound. The reaction generally requires an organic solvent alone or in admixture with water in that the coupled intermediate is generally not soluble in water alone. In the case where a protein is reacted with the coupled intermediate, the organic solvent should be one which does not adversely affect the protein (does not denature the protein; e.g., dimethylformamide, or dimethylsulfoxide).

The coupling agents of the present invention may be employed for coupling a wide variety of organic materials to each other. Thus, for example, the coupling compounds of the present invention may be employed for producing tracers which are to be used in an assay wherein such a tracer is comprised of a suitable marker; e.g., a radioactive marker, chromogen, enzyme, etc., coupled to a ligand (the term "ligand" as used herein refers to a hapten, antigen or antibody).

Similarly, the coupling agents of the present invention may be employed for coupling a ligand to a solid support, such as a polymer, for use in an assay.

The coupling agents of the present invention may also be employed for producing therapeutic materials, such as, for example, by coupling a therapeutic agent to an antibody for delivering the therapeutic agent to an antigenic site; e.g., in an animal.

Thus, in structural formula V, R may be an organic radical derived from organic compounds, which include an appropriate active hydrogen group of the type hereinabove described, which organic compound is preferably a chromogen (a dye, preferably a fluorescent dye), a non-protein antigen, a non-protein hapten, an enzyme, an organic compound, including a radioactive substituent group, a solid support, or a therapeutic agent (in particular, a drug).

Similarly, in structural formula V, X may be an organic radical derived from an organic compound having at least one primary amine substituent group, which organic compound may be a protein, an antibody, a hapten, an antigen, a chromogen (a dye, preferably a fluorescent dye), an enzyme, an organic compound having a radioactive substituent group, a polymer, etc.

Thus, for example, in producing a tracer for use in an assay in structural formula V, one of R and X is a ligand, and the other of R and X is a marker, such as a chromogen, an organic compound including a radioactive substituent group, or an enzyme. As hereinabove described, if the tracer is to be produced from a ligand which is a protein, in structural formula V, X is preferably derived from the protein, and R is derived from an organic compound capable of functioning as a marker.

Thus, for example, in producing a fluorescent tracer, one of R and X is derived from a fluorescent dye having an appropriate substituent group, which can be coupled to one of the functional groups of the coupling agent, whereas the other of R and X is a ligand.

The marker compound which is coupled by use of the coupling agents of the present invention, as herein above noted, may be an enzyme, a chromogen, or an organic compound containing a radioactive substituent group, such as radioactive iodine.

As representative examples of suitable chromogens, there may be mentioned: acridine dyes, azure dyes, quinone dyes, Nile Blue, Cresyl Violet fluoresceins, rhodamines, coumarines, amino naphthalene derivatives (dansyl compounds), etc.

As representative examples of suitable radioactive markers, there may be mentioned: hydrozyphenyl substituted amines or amino acids, wherein the phenyl group includes one or more radioactive substituent groups, such as radioiodinated tyrosine, or tyramine; imidazole substituted amino acids or amines wherein the imidazole group is substituted with one or more radioactive substituent groups.

As representative examples of suitable enzyme markers, there may be mentioned: peroxidases, β-galacosidase, acethylcholine esterase, glucoamilase, maleic acid dehydrogenase, glucose-6-phosphoric acid dehydrogenase, glutaroxidase, acid phosphatase, etc.

As known in the art, the solid support may be a polymer, provided that the polymer includes a substituent group capable of reacting with one of the reactive groups of the coupling compounds (I or II); e.g., polyacrylamide, poly (aminostyrene), cellulose, crosslined agarose, etc.

The tracers and supported ligands prepared in accordance with the present invention may be employed in an assay for a wide variety of analytes (the term "analyte" refers to a hapten, antigen or antibody), of a type generally known in the art. Thus, for example, the present invention is applicable to Assays for drugs, including therapeutic drugs and so-called "drugs of abuse"; steroids, vitamins, sugars, amino acids, polypeptides, proteins, various hormones, antibiotics, viruses, etc.

The tracers and supported ligands prepared in accordance with the present invention may be employed in an immunoassay (the term "immunoassay" is used in a generic sense and includes assays which use naturally occurring binders instead of an antigen or antibody, and which are sometimes referred to as competitive protein binding assays), and as known in the art, one of the components of the assay is a binder. In the case where the analyte is a hapten or antigen, the binder may be an antibody or naturally occurring substance which has one or more binding sites specific for the analyte, and in the case where the analyte is an antibody, the binder may be an antigen to the antibody or an antibody elicited in response to the analyte. The selection of a suitable binder is deemed to be within the scope of those skilled in the art, and no further details in this respect are deemed necessary for a complete understanding of the invention.

In the assay, the ligand portion of the tracer used in the assay is determined by the type of assay to be employed. Thus, for example, if the assay is for an analyte which is either the antigen or hapten, the ligand portion of the tracer is either the antigen or hapten to be assayed or appropriate analog thereof (the term "appropriate analog" means an analog of the analyte which is bound by the binder used in the assay). Alternatively, the ligand portion of the tracer may be a binder for the hapten or antigen to be assayed, in which case the assay is designed so that the analyte inhibits binding of the tracer to binding sites specific for the tracer.

In the case where the analyte is an antibody, the ligand portion of the trace may be the antibody or appropriate analog thereof, in which case both the antibody and the tracer would compete for limited number of binding sites specific for both the antibody analyte and the tracer. Alternatively, the ligand portion of the tracer may be an antigen to the antibody analyte or antibody elicited in response to the antibody analyte, in which case, the antibody analyte inhibits binding of the tracer to binding sites specific for the tracer.

In some cases, where the analyte is to be determined by a so-called "sandwich type" of assay, the ligand portion of the tracer has binding sites specific for the analyte, which analyte has multiple determinant sites.

The selection of a suitable ligand for use as the ligand portion of the tracer is deemed to be within the scope of those skilled in the art from the teachings herein and, accordingly, no further details in this respect are deemed necessary for a complete understanding of the present invention.

The coupling agents of the present invention may also be employed for coupling a therapeutic agent to an antibody, and in particlar monoclonal antibody. In such a case, in structural formula V, R is derived from a therapeutic agent, and X is derived from an antibody.

Thus, as should be apparent from the hereinabove description, the coupled compound V may be produced from a wide variety of organic compounds, with the organic radical represented by X in coupled compound V being derived from another organic compound, provided that the respective organic compounds include appropriate active hydrogen substituent groups. Thus, in the coupled compound V, R may be an organic radical derived from organic compounds which include an active hydrogen group capable of reacting with an isocyanate and/or isothiocyanate group, which organic compound may be a marker (radioactive substituted organic compound, a chromogen, preferably a fluorescent dye, an enzyme), or a ligand, and in particular, a non-protein antigen or a nonprotein hapten, a solid support or a therapeutic agent (in particular, a drug). Similarly, X may be an organic radical derived from an organic compound which includes a primary amine group. Thus, X may be an organic radical derived from an organic compound which may be a protein, antibody, a hapten, an antigen, a chromogen (a dye, preferably a fluorescent dye), an enzyme, an organic compound have a radioactive substituent group, a polymer, etc.

The present invention will be further described with respect to the following examples; however, the scope of the invention is not to be limited thereby:

EXAMPLE 1

To a mixture of 1 equivalent of α-amino-γ-butyrolactone in dry dioxane at room temperature under nitrogen 1.0 equivalent of phosgene is added. The resulting mixture is refluxed for 4 hours. After cooling the mixture is filtered and the solvent is removed under reduced pressure. The resulting oil (isocyanate) is not further purified, but used immediately for coupling.

The above procedure is used replacing phosgene with thiophosgene to produce Compound II wherein A is —N=C=S.

EXAMPLE 2

The procedure of Example 1 is repeated, replacing D, L-homocysteinethiolactone with D, L-homocysteme-thiolactone to produce Compound I wherein A is —N=C=S.

Example 2 is repeated replacing the phosgene with thiophosgenen to produce Compound I wherein A is —N=C=S.

EXAMPLE 3

The isocyanate derivative which is produced by the procedure of Example 1 or 2 is reacted in equal molar proportions with digoxin, in pyridine, in a nitrogen purged vessel at room temperature for 4 hours to produce either Compound III or IV wherein Y is

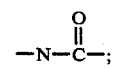

D is —O— and R is a digoxin radical.

EXAMPLE 4

The procedure is repeated employing the isothiocyanate derivative which is produced in Example 1 or 2 and thyroxine (T$_4$) to produce Compound III or IV where Y is

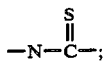

D is —NH— and R is a thyroxine radical.

EXAMPLE 5

A compound which is produced in Example 3 or 4 is reacted in equivalent proportions with fluorescein amine in water at pH 9.5 (inorganic buffer i.e. borate) at room temperature and pressure to produce coupled Compound V wherein X is a fluorescein radical and R, Y and D are as defined in Examples 3 and 4.

The same procedure may be employed for coupling compounds prepared as in Examples 3 and 4 with a protein by using the compound which is produced by the procedure of Example 3 and 4 in a molar excess with respect to protein; e.g., 25-30:1.

It is to be understood that the above procedures are also applicable to coupling of other ligands to other organics; for example, enzymes, polymers, etc.

The present invention is particularly advantageous in that it permits coupling of one organic to another in a rapid and simple manner. Moreover, by using a coupling agent with different functional groups it is possible to couple two different organic compounds by different reactions (different reaction linkages), thereby eliminating the tendency of crosslinking in each of the separate coupling reactions.

These and other advantages should be apparent to those skilled in the art, from the teachings herein.

Numerous modifications and variations of the present invention ar possible in light of the above teachings and, therefore, within the scope of the appended claims, the invention may be practied otherwise than as described.

What is claimed is:

1. A compound having the following structural formula:

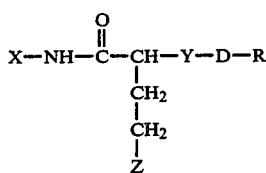

wherein
one of R and X is a ligand and the other of R and X is selected from the group consisting of detectable markers, solid supports and therapeutic drugs and when one of R and X is a therapeutic drug, the other of R and X is an antibody,
Z is selected from the group consisting of —SH and —OH
Y is selected from the group consisting of

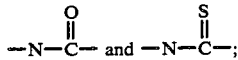

when Y is

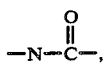

D is selected from the group consisting of —O—, —S—,

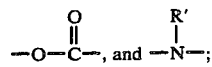

and
when Y is

and R' is selected from the group consisting of hydrogen and hydrocarbon radicals.

2. The compound of claim 1 wherein R is a ligand selected from the group consisting of haptens and antigens.

3. The compound of claim 2 wherein X is a detectable marker.

4. The compound of claim 3 wherein the marker is a fluorescent dye.

5. The compound of claim 4 wherein the marker is a fluorescein dye.

6. The compound of claim 3 wherein R is a digoxin radical, Y is

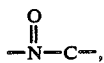

and D is —O—.

7. The compound of claim 6 wherein X is a fluorescent dye.

8. The compound of claim 7 wherein X is a fluorescein dye.

9. The compound of claim 3 wherein R is a T$_4$ radical, Y is

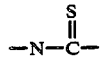

and D is —NH—.

10. The compound of claim 3 wherein X is a fluorescent dye.

11. The compound of claim 4 wherein X is a fluorescein dye.

12. The compound of claim 1 wherein one of R and X is a detectable marker and the other of R and X is a ligand selected from the group consisting of antigens, haptens and antibodies.

13. The compound of claim 2 wherein X is an enzyme.

14. The compound of claim 2 wherein X is an organic compound having a radioactive substituent group.

15. In an assay for an analyte which uses a tracer, the improvement comprising:
contacting at least one of an analyte and a binder for the analyte with a tracer which is the compound of claim 3.

16. In an assay for an analyte which uses a tracer, the improvement comprising:
  contacting at least one of an analyte and a binder for the analyte with a tracer which is the compound of claim 4.

17. In an assay for an analyte which uses a tracer, the improvement comprising:
  contacting at least one of an analyte and a binder for the analyte with a tracer which is the compound of claim 6.

18. In an assay for an analyte which uses a tracer, the improvement comprising:
  contacting at least one of an anlayte and a binder for the analyte with a tracer which is the compound of claim 9.

* * * * *